US012661021B2

(12) United States Patent
Ezoe et al.

(10) Patent No.: US 12,661,021 B2
(45) Date of Patent: Jun. 23, 2026

(54) SPHYGMOMANOMETER, BLOOD PRESSURE MEASUREMENT METHOD, AND COMPUTER-READABLE RECORDING MEDIUM

(71) Applicant: OMRON HEALTHCARE CO., LTD., Muko (JP)

(72) Inventors: Mika Ezoe, Kyoto (JP); Shingo Yamashita, Kyoto (JP); Yasuo Asano, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 732 days.

(21) Appl. No.: 18/148,511

(22) Filed: Dec. 30, 2022

(65) Prior Publication Data

US 2023/0143560 A1     May 11, 2023

Related U.S. Application Data

(63) Continuation of application No. PCT/JP2021/025467, filed on Jul. 6, 2021.

(30) Foreign Application Priority Data

Jul. 27, 2020    (JP) ................................. 2020-126438

(51) Int. Cl.
*A61B 5/0235* (2006.01)
*A61B 5/00* (2006.01)
*A61B 5/022* (2006.01)

(52) U.S. Cl.
CPC ............ *A61B 5/0235* (2013.01); *A61B 5/022* (2013.01); *A61B 5/7221* (2013.01)

(58) Field of Classification Search
CPC ..... A61B 5/0235; A61B 5/022; A61B 5/7221; A61B 5/6824; A61B 5/02225;

(Continued)

(56) References Cited

U.S. PATENT DOCUMENTS 4,271,843 A  *  6/1981  Flynn ................. A61B 5/02225
                                                    600/494
8,753,283 B2 *  6/2014  Leschinsky ........ A61B 5/02233
                                                    600/490

(Continued)

FOREIGN PATENT DOCUMENTS

CN          102266632 A     12/2011
CN          203672610 U  *  6/2014

(Continued)

OTHER PUBLICATIONS

Mar. 14, 2025 Office Action issued in Chinese Patent Application No. 202180048088.2.

(Continued)

*Primary Examiner* — Jacqueline Cheng
*Assistant Examiner* — Jonathan E. Cooper
(74) *Attorney, Agent, or Firm* — Oliff PLC

(57)                    ABSTRACT

A sphygmomanometer according to the present invention includes a pump that supplies a fluid to a blood pressure measurement cuff, a pressure sensor that detects a pressure of the cuff, a first valve for regular measurement, and a second valve for emergency exhaust. A blood pressure measurement unit measures a blood pressure of a measurement target site by controlling operations of the pump and the first and second valves on the basis of the pressure of the cuff. The abnormality determination unit supplies the fluid to the cuff by the pump in a state where a closing instruction is given to the first valve and an opening instruction is given to the second valve, and determines whether or not there is an abnormality in an emergency exhaust function according to a degree of increase in the pressure of the cuff.

12 Claims, 9 Drawing Sheets

(58) Field of Classification Search
  CPC .... A61B 2560/0276; A61B 2562/0247; A61B 5/02108; A61B 5/746; A61B 5/02141
  USPC ........................................................ 600/490
  See application file for complete search history.

(56) References Cited

U.S. PATENT DOCUMENTS

| | | | |
|---|---|---|---|
| 2012/0203119 A1 | 8/2012 | Yamashita et al. | |
| 2017/0293727 A1* | 10/2017 | Klaassen ................ | G16H 40/67 |
| 2021/0022628 A1* | 1/2021 | Telfort ................... | A61B 5/259 |
| 2021/0315466 A1* | 10/2021 | Ono ....................... | A61B 5/681 |

FOREIGN PATENT DOCUMENTS

| | | | |
|---|---|---|---|
| JP | S57-173038 A | 10/1982 | |
| JP | S60-163635 A | 8/1985 | |
| JP | H02-21843 A | 1/1990 | |
| JP | H03-23837 A | 1/1991 | |
| JP | H7-178065 A | 7/1995 | |
| JP | 2002-034938 A | 2/2002 | |
| JP | 2018-102872 A | 7/2018 | |
| JP | 2020-103638 A | 7/2020 | |
| WO | 2011055716 A1 | 5/2011 | |
| WO | WO-2020137480 A1 * | 7/2020 | ........... A61B 5/0235 |

OTHER PUBLICATIONS

Sep. 28, 2021 International Search Report Issued In International Application No. PCT/JP2021/025467.
Jul. 1, 2025 Examination Report issued in Indian Patent Application No. 202217071082.

* cited by examiner

SITTING POSITION

SUPINE POSITION

SPHYGMOMANOMETER, BLOOD PRESSURE MEASUREMENT METHOD, AND COMPUTER-READABLE RECORDING MEDIUM

CROSS-REFERENCE TO RELATED APPLICATION

This application is based on an application No. 2020-126438 filed in Japan on Jul. 27, 2020, the entire content of which is hereby incorporated by reference.

TECHNICAL FIELD

The present invention relates to a sphygmomanometer, and more specifically to a sphygmomanometer that performs blood pressure measurement by temporarily compressing a measurement target site by a blood pressure measurement cuff. Furthermore, the present invention relates to a blood pressure measurement method for measuring a blood pressure by such a sphygmomanometer. Furthermore, the present invention relates to a computer-readable recording medium storing a program for causing a computer to execute such a blood pressure measurement method.

BACKGROUND ART

Conventionally, as this type of sphygmomanometer, for example, as disclosed in Patent Literature 1 (JP H03-23837 A), there has been known a sphygmomanometer including: a cuff (band) that compresses a living body; a measurement control unit that controls an operation of blood pressure measurement; a leak valve that leaks air from a pressurizing tube connected to the cuff during the blood pressure measurement; an emergency relief valve for relieving the pressurizing tube connected to the cuff in case of emergency; a safety control unit that operates the emergency relief valve in a case where the measurement control unit does not output a signal indicating measurement completion even after a lapse of a predetermined time after starting measurement. Furthermore, Patent Literature 1 discloses that an accident is prevented by confirming whether or not a power supply voltage value can be normally supplied to the measurement control unit and the safety control unit before starting measurement.

SUMMARY OF INVENTION

In Patent Literature 1, whether or not the power supply voltage value can be normally supplied is confirmed before starting the measurement, but the operation of the emergency relief valve is not confirmed. For this reason, in a case where the emergency relief valve itself has been failed, there is a problem that exhaust in an emergency (in case of emergency) is not performed. For example, in a sphygmomanometer such as a nighttime sphygmomanometer that starts measurement of a blood pressure according to a schedule set in advance while a subject is sleeping (night-time), if the emergency relief valve is failed in case of emergency, a measurement target site is compressed for a long time while the subject is unconscious, and a state occurs in which an artery remains in an ischemic condition.

Therefore, an object of the present invention is to provide a sphygmomanometer and a blood pressure measurement method capable of reliably preventing occurrence of a state where a measurement target site remains compressed for a long time. Furthermore, an object of the present invention is to provide a computer-readable recording medium storing a program for causing a computer to execute such a blood pressure measurement method.

In order to achieve the object, a sphygmomanometer of the present disclosure is a sphygmomanometer that performs blood pressure measurement by temporarily compressing a measurement target site by a blood pressure measurement cuff, the sphygmomanometer comprising:

a pump that supplies a fluid to the cuff to pressurize the cuff;

a pressure sensor that detects a pressure of the cuff;

a first valve for regular measurement that discharges the fluid from the cuff to depressurize the cuff during blood pressure measurement;

a second valve for emergency exhaust that discharges the fluid from the cuff to depressurize the cuff when an abnormality occurs in which discharge of the fluid by the first valve is not normally performed;

a blood pressure measurement unit that controls operations of the pump and the first and second valves on a basis of the pressure of the cuff output from the pressure sensor to measure a blood pressure of the measurement target site; and an abnormality determination unit that performs a determination process of supplying the fluid to the cuff by the pump in a state where a closing instruction is given to the first valve and an opening instruction is given to the second valve, and determining whether or not there is an abnormality in an emergency exhaust function according to a degree of increase in the pressure of the cuff.

In this specification, giving a "closing instruction" to a valve refers to controlling the valve to close regardless of whether the valve type is a normally open valve or a normally closed valve. Furthermore, giving an "opening instruction" to a valve refers to controlling the valve to open regardless of whether the valve type is a normally open valve or a normally closed valve.

In another aspect, a blood pressure measurement method of the present disclosure is a blood pressure measurement method for performing blood pressure measurement by temporarily compressing a measurement target site by a blood pressure measurement cuff, comprising:

a pump that supplies a fluid to the cuff to pressurize the cuff;

a pressure sensor that detects a pressure of the cuff;

a first valve for regular measurement that discharges the fluid from the cuff to depressurize the cuff during blood pressure measurement; and a second valve for emergency exhaust that discharges the fluid from the cuff to depressurize the cuff when an abnormality occurs in which discharge of the fluid by the first valve is not normally performed, the blood pressure measurement method comprising:

a measurement step of measuring a blood pressure of the measurement target site by controlling operations of the pump and the first and second valves on a basis of the pressure of the cuff output from the pressure sensor; and a determination step of supplying the fluid to the cuff by the pump in a state where a closing instruction is given to the first valve and an opening instruction is given to the second valve, and determining whether or not there is an abnormality in an emergency exhaust function according to a degree of increase in the pressure of the cuff, as a step performed prior to the measurement step each time the measurement step is performed.

In yet another aspect, a computer-readable recording medium according to the present disclosure is a non-transitorily computer-readable recording medium storing a program for causing a computer to execute the above blood pressure measurement method.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, an embodiment of the present invention will be described in detail with reference to the drawings.
(Configuration of Sphygmomanometer)

Figure 1:
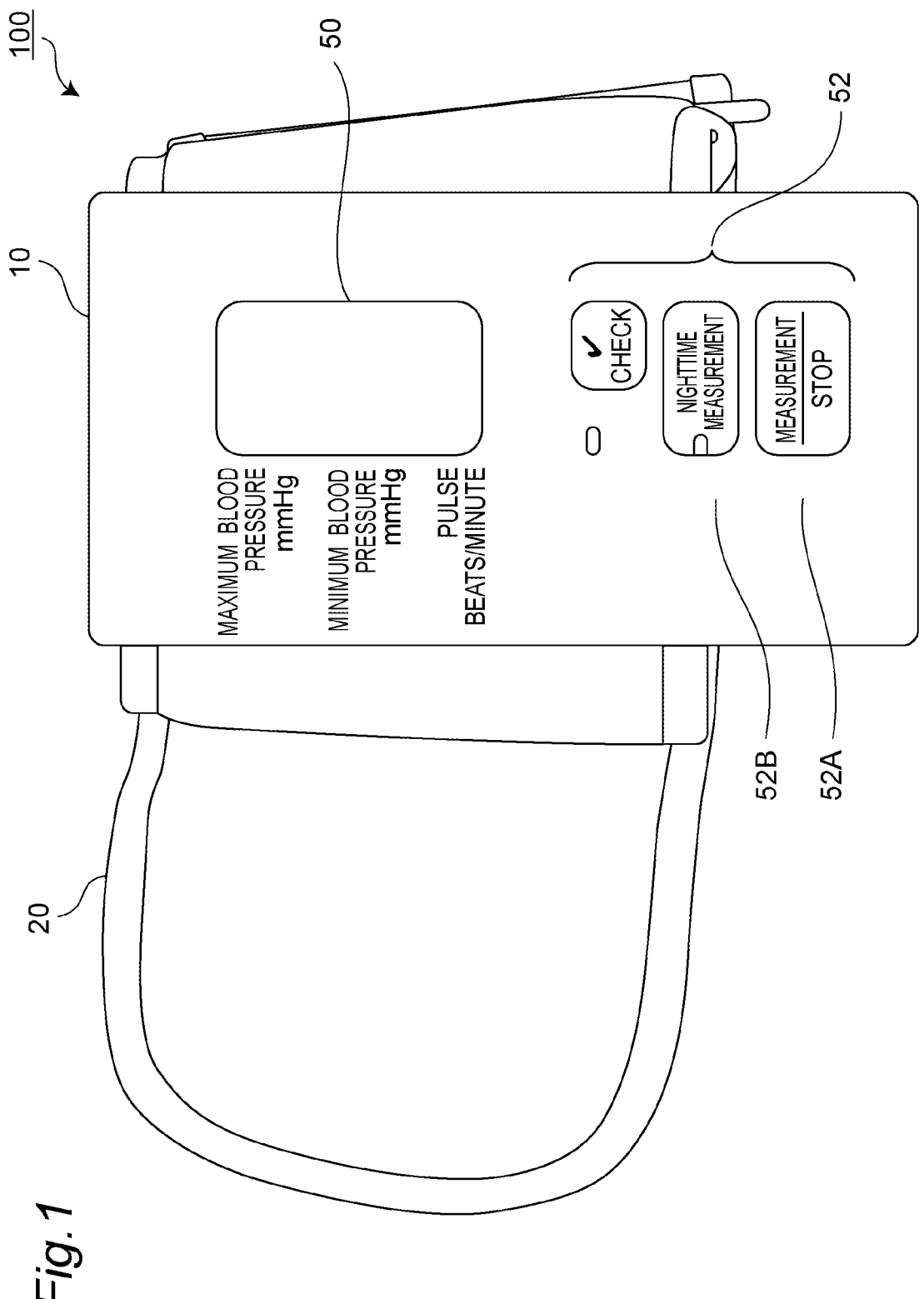
FIG. 1 is a view illustrating an external appearance of a wrist-type sphygmomanometer according to one embodiment of the present invention.

FIG. 1 illustrates an external appearance of a wrist-type sphygmomanometer 100 according to one embodiment of the present invention. The sphygmomanometer 100 roughly includes a blood pressure measurement cuff 20 that is to be worn on a left wrist 90 (see FIG. 3 described later) as a measurement target site, and a main body 10 that is integrally attached to the cuff 20.

The cuff 20 is a general one for a wrist-type sphygmomanometer, and has an elongated band shape so as to surround the left wrist 90 along its circumferential direction. The cuff 20 includes a fluid bag 22 (see FIG. 2) therein for compressing the left wrist 90. Note that, in order to maintain the cuff 20 in an annular shape at all times, a curler having appropriate flexibility may be provided in the cuff 20.

Figure 3:
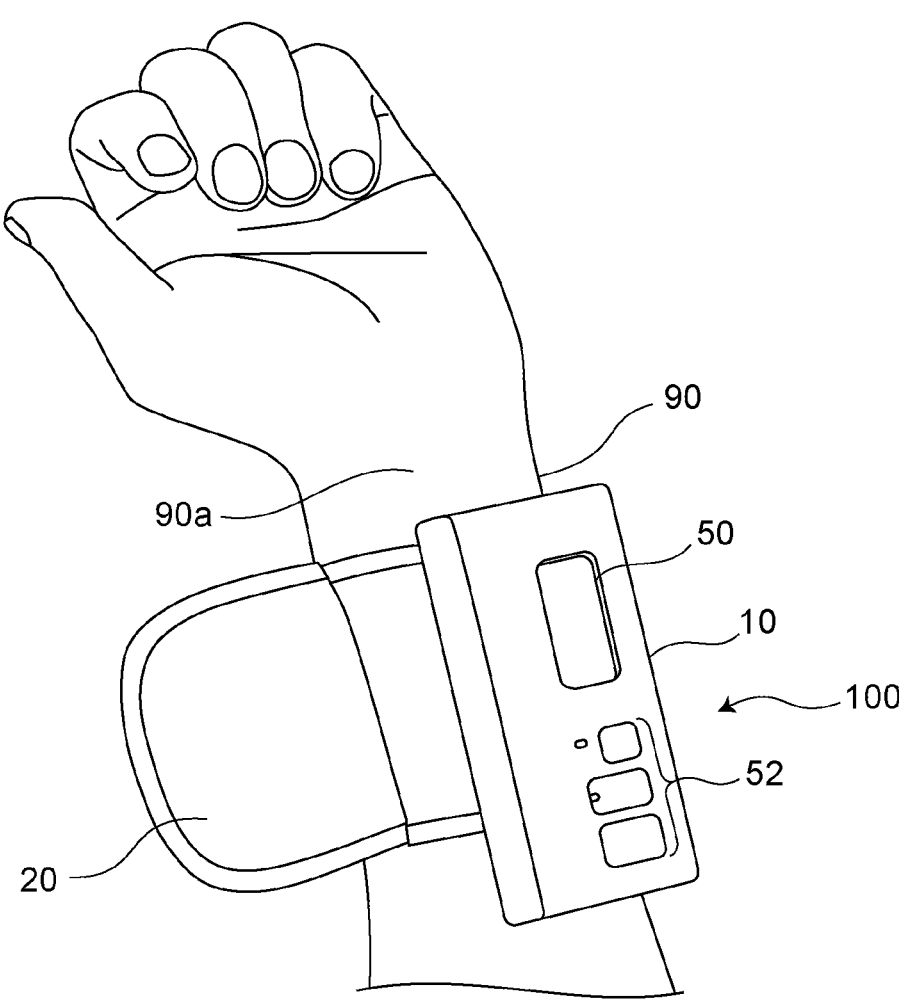
FIG. 3 is a view illustrating a mode in which the sphygmomanometer is worn on a left wrist as a measurement target site.

As illustrated in FIG. 3, the main body 10 is integrally attached to a substantially center portion in a longitudinal direction of the band-shaped cuff 20. In this example, the portion to which the main body 10 is attached is supposed to correspond to a palm-side surface (surface on a palm side of a hand) 90a of the left wrist 90 in a worn state.

The main body 10 has a flat substantially rectangular parallelepiped shape along an outer peripheral surface of the cuff 20. The main body 10 is formed to be small and thin so as not to disturb the sleep of a user (in this example, referring to a subject, and the same applies hereinafter). Furthermore, corner portions of the main body 10 are rounded (the corners are rounded).

As illustrated in FIG. 1, the main body 10 is provided with, on a surface (top surface) on a side farthest from the left wrist 90 among outer surfaces thereof, a display 50 forming a display screen and an operation unit 52 for inputting an instruction from the user.

In this example, the display 50 is constituted of a liquid crystal display (LCD), and displays given information according to a control signal from a central processing unit (CPU) 110 described later. In this example, a maximum blood pressure (unit; mmHg), a minimum blood pressure (unit; mmHg), and a pulse (unit; beats/minute) are displayed. Note that the display 50 may be constituted of an organic electro luminescence (EL) display, or may include a light emitting diode (LED).

The operation unit 52 inputs an operation signal corresponding to an instruction from the user to the CPU 110 described later. In this example, the operation unit 52 includes a measurement switch 52A as a measurement instruction input unit for receiving a blood pressure measurement instruction from the user, and a nighttime measurement switch 52B as a mode operation unit for receiving an instruction to switch a mode between a regular blood pressure measurement mode and a nighttime blood pressure measurement mode. Here, the "regular blood pressure measurement mode" means a mode in which, when a blood pressure measurement instruction is input through the measurement switch 52A, blood pressure measurement is performed in response to the blood pressure measurement instruction (however, as described later, the absence of an abnormality in an emergency exhaust function may be set as a condition for starting the blood pressure measurement). The "nighttime blood pressure measurement mode" means a mode (automatic measurement mode) in which blood pressure measurement is automatically started according to a schedule set in advance so that blood pressure values can be measured while the user is sleeping (however, as described later, the absence of an abnormality in the emergency exhaust function may be set as a condition for starting the blood pressure measurement). The schedule set in advance refers to a plan to measure at, for example, fixed clock times such as 1:00, 2:00, or 3:00, in the middle of the night, or a plan to measure, for example, once every two hours after the nighttime measurement switch 52B being pressed.

Specifically, in this example, each of the measurement switch 52A and the nighttime measurement switch 52B is a momentary type (self-return type) switch, and is in an on-state only while being pressed down, and returns to an off-state when being released.

When the measurement switch 52A is once pressed down while the sphygmomanometer 100 is in the regular blood pressure measurement mode, which means a blood pressure measurement instruction, the measurement target site (left wrist 90) is temporarily compressed by the cuff 20, and blood pressure measurement is executed by an oscillometric method. When the measurement switch 52A is pressed down again during the blood pressure measurement (for example, during pressurization of the cuff 20), which means an instruction to stop the blood pressure measurement, the blood pressure measurement is immediately stopped.

When the nighttime measurement switch 52B is once pressed down while the sphygmomanometer 100 is in the regular blood pressure measurement mode, which means an instruction to transition to the nighttime blood pressure measurement mode, the sphygmomanometer 100 transitions from the regular blood pressure measurement mode to the nighttime blood pressure measurement mode (however, as described later, the absence of an abnormality in the emergency exhaust function may be set as a transition condition to the nighttime blood pressure measurement mode). In the nighttime blood pressure measurement mode, as described above, blood pressure measurement by the oscillometric method is automatically started according to the schedule set in advance. When the nighttime measurement switch 52B is pressed down again while the sphygmomanometer 100 is in the nighttime blood pressure measurement mode, which means an instruction to stop the nighttime blood pressure measurement mode, the sphygmomanometer 100 transitions from the nighttime blood pressure measurement mode to the regular blood pressure measurement mode.

Figure 2:
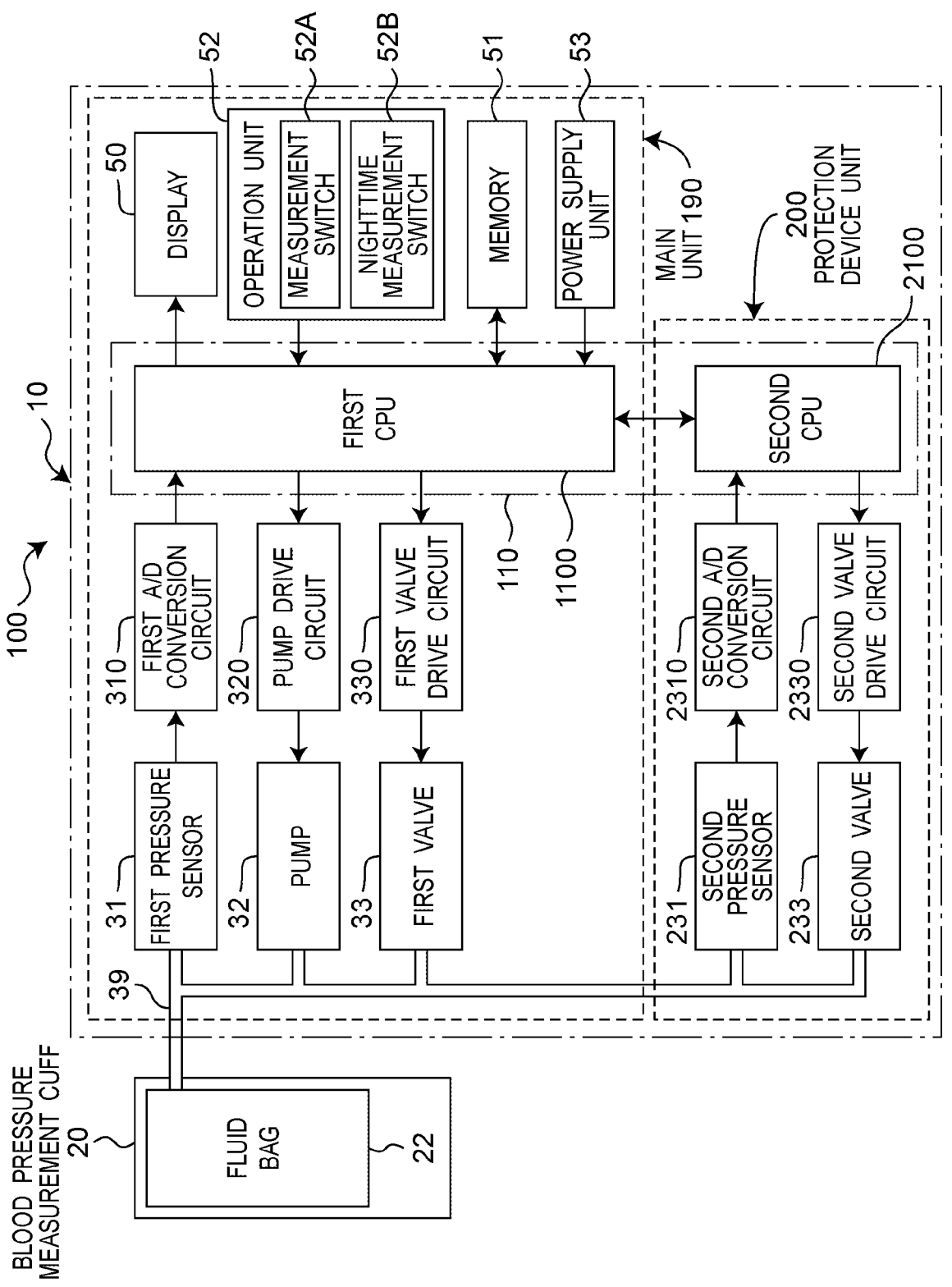
FIG. 2 is a diagram illustrating a block configuration of the sphygmomanometer.

FIG. 2 illustrates a block configuration of the sphygmomanometer 100.

As described above, the cuff 20 includes the fluid bag 22 for compressing the left wrist 90 as the measurement target site. The fluid bag 22 and the main body 10 are connected by an air pipe 39 so as to be capable of fluid communication.

The main body 10 is roughly equipped with a main unit 190 for blood pressure measurement and a protection device unit 200 for emergency exhaust.

The main unit 190 includes, in addition to the display 50 and the operation unit 52 described above, a first CPU 1100 that constitutes a part of the CPU 110 as a control unit, a memory 51 as a storage unit, a power supply unit 53, a first pressure sensor 31, a pump 32, and a first valve 33 for blood pressure measurement. Furthermore, the main unit 190 includes a first A/D conversion circuit 310 that converts an output of the first pressure sensor 31 from an analog signal to a digital signal, a pump drive circuit 320 that drives the pump 32, and a first valve drive circuit 330 that drives the first valve 33.

The protection device unit 200 includes a second CPU 2100 that constitutes a part of the CPU 110 as the control unit, a second pressure sensor 231, a second valve 233 for emergency exhaust, a second A/D conversion circuit 2310 that converts an output of the second pressure sensor 231 from an analog signal to a digital signal, and a second valve drive circuit 2330 that drives the second valve 233.

The first pressure sensor 31, the pump 32, the first valve 33, the second pressure sensor 231, and the second valve 233 are commonly connected to the fluid bag 22 through the air pipe 39 so as to be capable of fluid communication.

The CPU 110 includes the first CPU 1100 as a first processor that mainly works for blood pressure measurement, and the second CPU 2100 as a second processor that mainly works for emergency exhaust, and controls the entire operation of the sphygmomanometer 100. Specifically, the CPU 110 works as a pressure control unit according to a program for controlling the sphygmomanometer 100 stored in the memory 51, and performs control to drive the pump 32, the first valve 33, and the second valve 233 in response to operation signals from the operation unit 52. Furthermore, the CPU 110, particularly the first CPU 1100 works as a blood pressure measurement unit, calculates blood pressure values by using an algorithm for blood pressure calculation by the oscillometric method, and controls the display 50 and the memory 51. The CPU 110, particularly the second CPU 2100 works as an abnormality determination unit, and confirms an operation of the protection device unit 200.

The memory 51 stores a program for controlling the sphygmomanometer 100, data used for controlling the sphygmomanometer 100, setting data for setting various functions of the sphygmomanometer 100, measurement result data of blood pressure values, and the like. Furthermore, the memory 51 is used as a work memory or the like when the program is executed.

In this example, the power supply unit 53 is constituted of a secondary battery, and supplies power to each unit of the CPU 110, the first pressure sensor 31, the pump 32, the first valve 33, the display 50, the memory 51, the first A/D conversion circuit 310, the pump drive circuit 320, the first valve drive circuit 330, the second pressure sensor 231, the second valve 233, the second A/D conversion circuit 2310, and the second valve drive circuit 2330.

The pump 32 supplies air as a fluid to the fluid bag 22 through the air pipe 39 in order to pressurize the pressure (cuff pressure) in the fluid bag 22 included in the cuff 20. The pump drive circuit 320 drives the pump 32 on the basis of a control signal given from the CPU 110.

In this example, the first valve 33 is constituted of a normally open solenoid valve, and is opened and closed to discharge the air in the fluid bag 22 or to fill the air into the fluid bag 22 through the air pipe 39 in order to control the cuff pressure. The first valve drive circuit 330 opens and closes the first valve 33 on the basis of a control signal given from the first CPU 1100. If the first valve 33 is normal, the first valve 33 becomes an open state upon receiving an opening instruction (de-energization), and becomes a closed state upon receiving a closing instruction (energization).

The first pressure sensor 31 and the first A/D conversion circuit 310 work as a pressure detection unit that detects the pressure of the cuff. In this example, the first pressure sensor 31 is a piezoresistive pressure sensor that detects the pressure (cuff pressure) in the fluid bag 22 included in the cuff 20 through the air pipe 39, and outputs it as electrical resistance due to the piezoresistive effect. The first A/D conversion circuit 310 converts the output (electrical resistance) of the first pressure sensor 31 from an analog signal to a digital signal, and outputs the digital signal to the CPU 110. In this example, the first CPU 1100 works as an oscillation circuit that oscillates at a frequency corresponding to the electrical resistance from the first pressure sensor 31, and acquires a signal indicating the cuff pressure according to the oscillation frequency.

In this example, the second valve 233 is constituted of a normally closed solenoid valve, and is opened in order to perform emergency exhaust of the air in the fluid bag 22 through the air pipe 39 in an emergency (in case of emergency). The second valve drive circuit 2330 opens and closes the second valve 233 on the basis of a control signal given from the second CPU 2100. If the second valve 233 is normal, the second valve 233 becomes an open state upon receiving an opening instruction (energization), and becomes a closed state upon receiving a closing instruction (de-energization).

The second pressure sensor 231 and the second A/D conversion circuit 2310 work as a pressure detection unit that detects the pressure of the cuff. In this example, the second pressure sensor 231 is a piezoresistive pressure sensor that detects the pressure (cuff pressure) in the fluid bag 22 included in the cuff 20 through the air pipe 39, and outputs it as electrical resistance due to the piezoresistive effect. The second A/D conversion circuit 2310 converts the output (electrical resistance) of the second pressure sensor 231 from an analog signal to a digital signal, and outputs the digital signal to the CPU 110. In this example, the second CPU 2100 works as an oscillation circuit that oscillates at a frequency corresponding to the electrical resistance from the second pressure sensor 231, and acquires a signal indicating the cuff pressure according to the oscillation frequency.

Figure 4A:
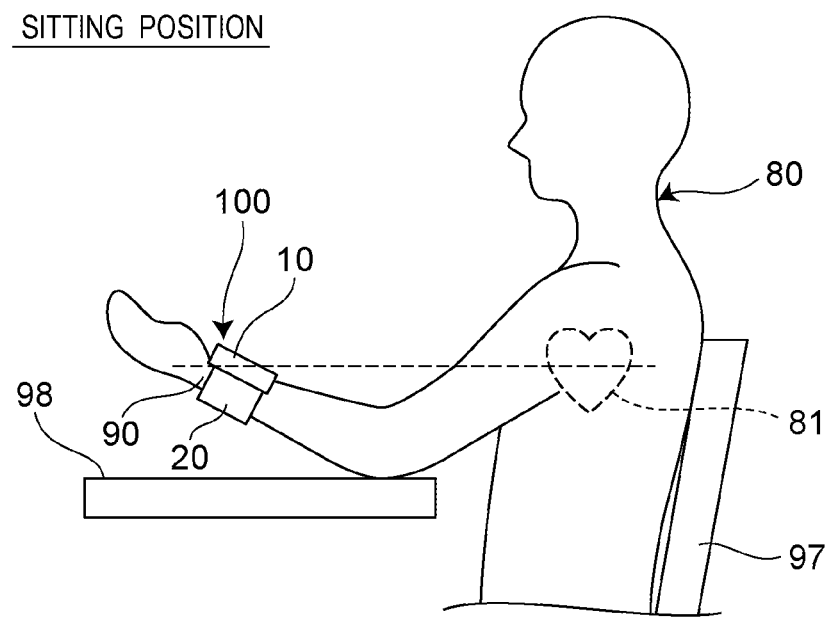
FIG. 4A is a view illustrating a sitting position as a measurement posture.
Figure 4B:
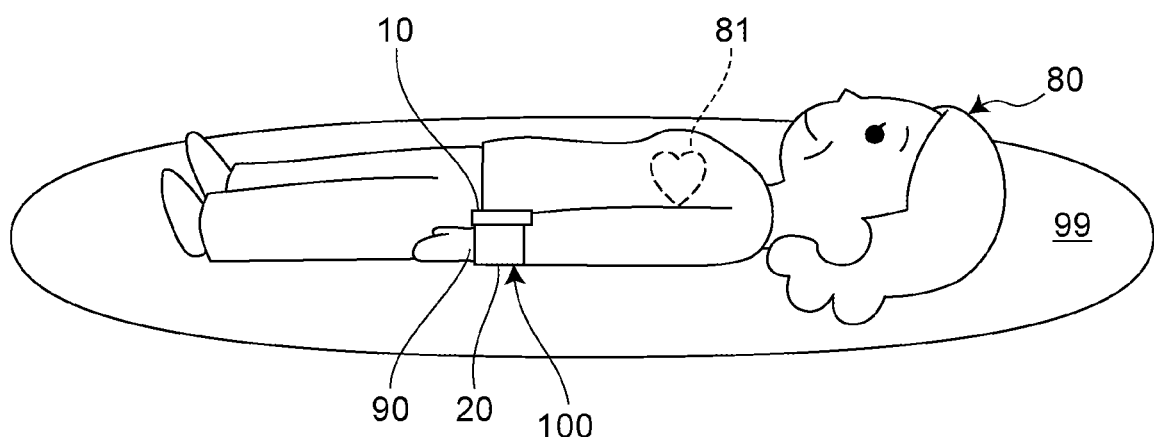
FIG. 4B is a view illustrating a supine position as a measurement posture.

FIGS. 4A and 4B illustrate measurement postures of "sitting position" and "supine position", respectively, which are recommended in a case where a subject performs blood pressure measurement by using the sphygmomanometer 100. Here, as illustrated in FIG. 4A, the "sitting position" means a posture in which a user 80 wearing the sphygmomanometer 100 on the left wrist 90 sits on a chair 97 or the like, and holds the left wrist 90 (and the sphygmomanometer 100) at a height level of a heart 81 by raising the left wrist 90 obliquely (the hand is up, the elbow is down) in front of a body trunk with the left elbow placed on a table 98. This posture eliminates the height difference between the left wrist 90 and the heart 81 of the user 80, and thus is recommended in order to increase the blood pressure measurement accuracy in the regular blood pressure measurement mode. On the other hand, as illustrated in FIG. 4B, the "supine position" means a posture in which the user 80 wearing the sphygmomanometer 100 on the left wrist 90 lies on his/her back on a horizontal floor surface 99 or the like in a state where the left elbow is extended along the body trunk. In the nighttime blood pressure measurement mode, blood pressure measurement is started according to the schedule set in advance while the subject is sleeping (nighttime), so that the subject is supposed to take the measurement posture of the "supine position".

(Blood Pressure Measurement Method)

Figure 5:
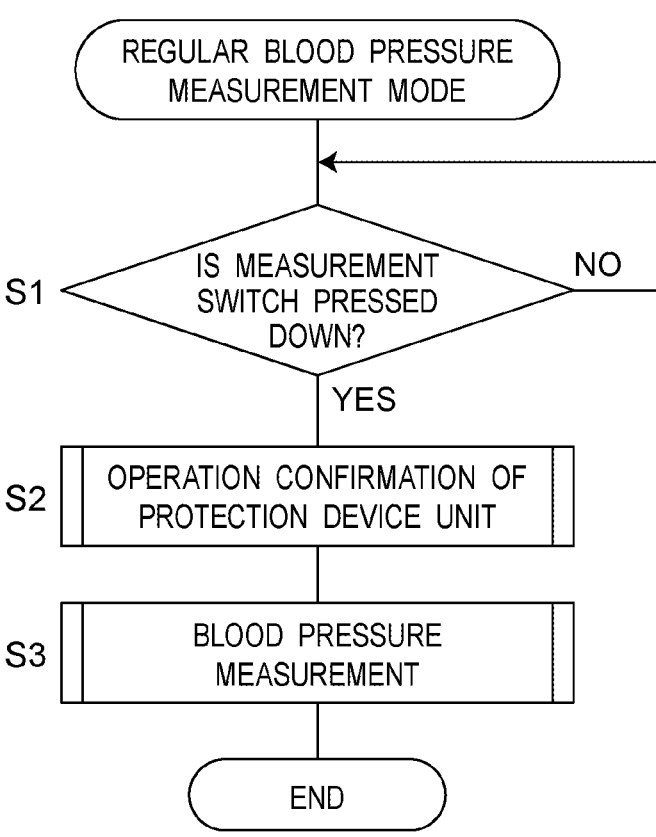
FIG. 5 is a diagram illustrating an operation flow in a case where the sphygmomanometer confirms an operation of a protection device unit in a regular blood pressure measurement mode.
Figure 6:
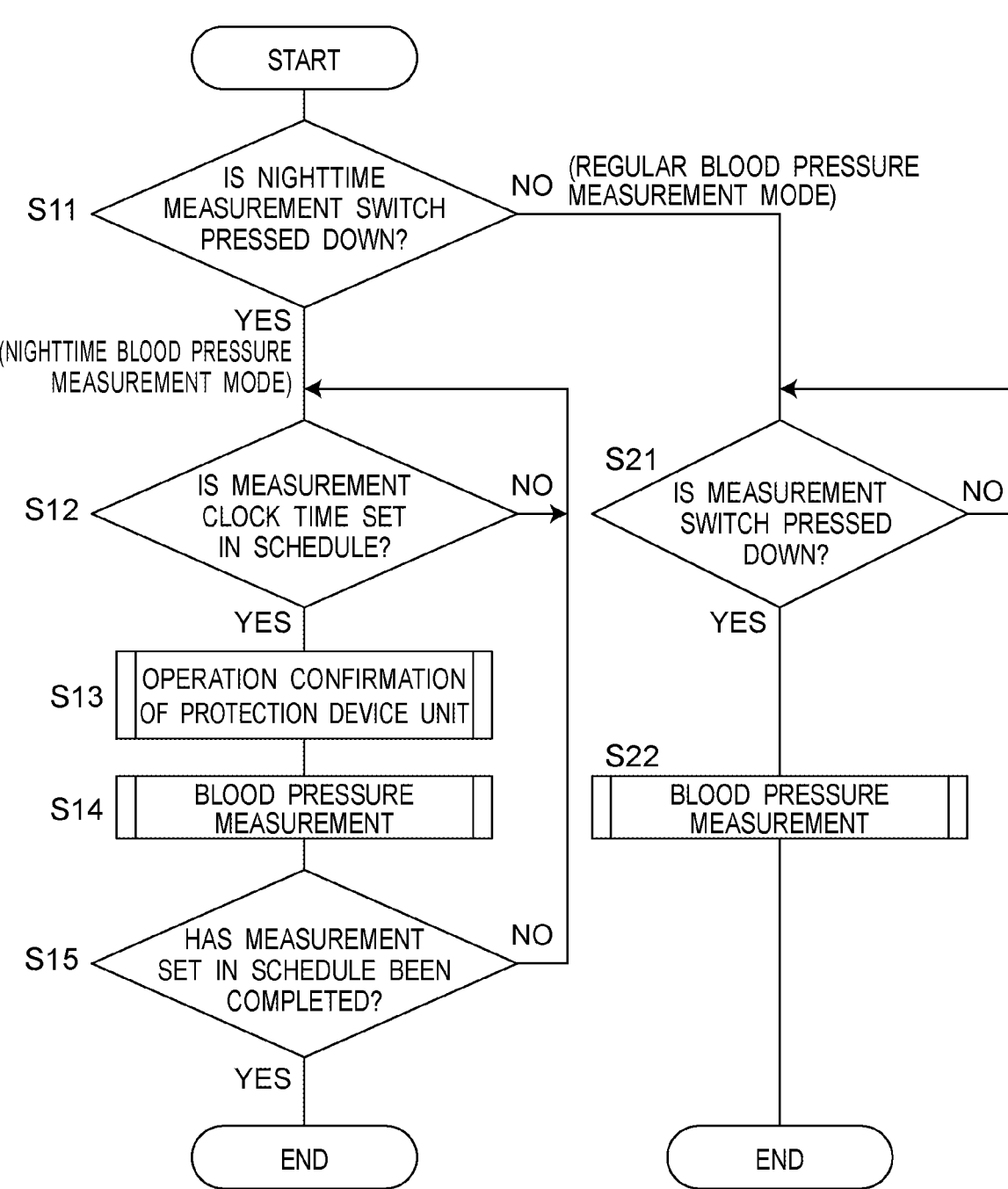
FIG. 6 is a diagram illustrating an operation flow in a case where the sphygmomanometer performs determination of the presence or absence of an abnormality of an emergency exhaust function only in a nighttime blood pressure measurement mode.

In the sphygmomanometer 100, there are a case where determination of the presence or absence of an abnormality of the emergency exhaust function is performed in the regular blood pressure measurement mode (an operation flow in FIG. 5), and apart from the case, a case where determination of the presence or absence of an abnormality of the emergency exhaust function is performed only in the nighttime blood pressure measurement mode (an operation flow in FIG. 6). Note that, hereinafter, the first CPU 1100 and the second CPU 2100 are collectively referred to as the CPU 110 except a case where they are specifically distinguished from each other.

(Case where Abnormality Determination of Emergency Exhaust Function is Performed in Regular Blood Pressure Measurement Mode)

FIG. 5 illustrates an operation flow in a case where the sphygmomanometer 100 performs determination of the presence or absence of the abnormality of the emergency exhaust function in the regular blood pressure measurement mode. Note that, in this example, when the measurement switch 52A is pressed in a power-off state, the power is turned on and the regular blood pressure measurement mode is set by default.

As illustrated in FIG. 4A, it is assumed that the user 80 wearing the sphygmomanometer 100 on the left wrist 90 is in a posture of the sitting position.

In this state, as shown in step S1 in FIG. 5, when the user presses down the measurement switch 52A provided on the main body 10 to input a blood pressure measurement instruction (YES in step S1), the CPU 110 proceeds to step S2 and enters into an operation confirmation routine of the protection device unit.

(Operation Confirmation Routine of Protection Device Unit)

Figure 8:
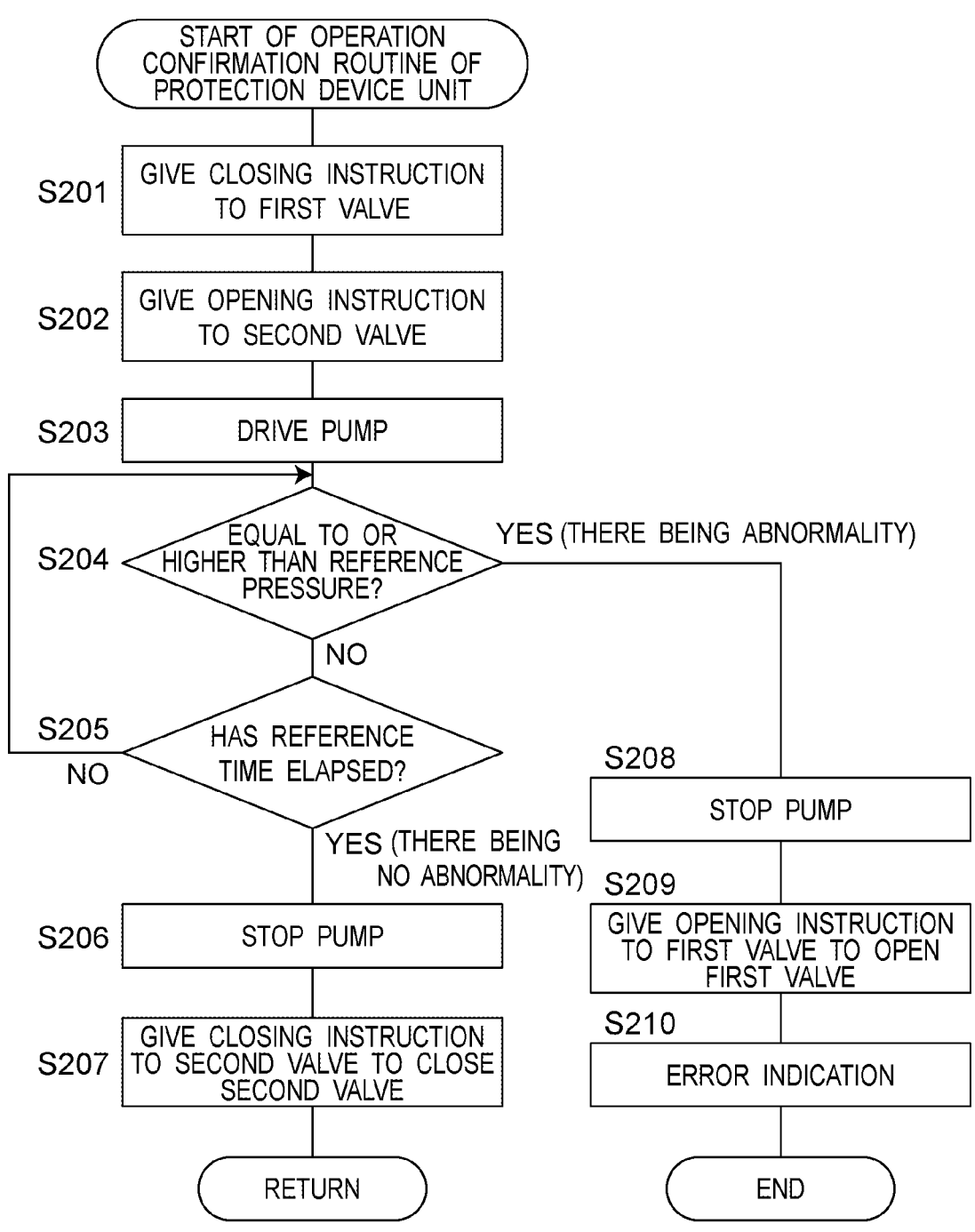
FIG. 8 is a diagram illustrating a specific flow of an operation confirmation routine of the protection device unit in the operation flows in FIGS. 5 and 6.

Specifically, in the operation confirmation routine of the protection device unit, as illustrated in FIG. 8, the CPU 110 gives a closing instruction (energization) to the first valve 33 via the first valve drive circuit 330 (step S201), and gives an opening instruction (energization) to the second valve 233 via the second valve drive circuit 2330 (step S202). In this state, the CPU 110 drives the pump 32 via the pump drive circuit 320, and supplies air to the cuff 20 (fluid bag 22) through the air pipe 39 (step S203). Then, the CPU 110 works as an abnormality determination unit, and performs a determination process of determining whether or not there is an abnormality in the emergency exhaust function according to the degree of increase in the pressure of the cuff 20 (steps S204 and S205).

Specifically, the CPU 110, particularly the second CPU 2100 determines whether or not the cuff pressure is equal to or higher than a reference pressure Pref (in this example, Pref=5 mmHg) on the basis of an output of the second pressure sensor 231 (step S204). Here, if the cuff pressure is less than the reference pressure Pref (NO in step S204), the determination as to whether or not the cuff pressure is equal to or higher than the reference pressure Pref is continued until a reference time tref (in this example, tref=5 sec) elapses from the start of driving of the pump 32 (steps S204 and S205). Then, when the cuff pressure becomes equal to or higher than the reference pressure Pref by the time at which the reference time tref elapses from the start of driving of the pump 32 (YES in step S204), it is determined that there is an abnormality in the emergency exhaust function. On the other hand, if the cuff pressure is less than the reference pressure Pref until the reference time tref elapses from the start of driving of the pump 32 (YES in step S205), it is determined that there is no abnormality in the emergency exhaust function. Note that the value of the reference time tref and the value of the reference pressure Pref can each be variably set.

The reason for performing the determination process (steps S204 and S205) is as follows.

Figure 9:
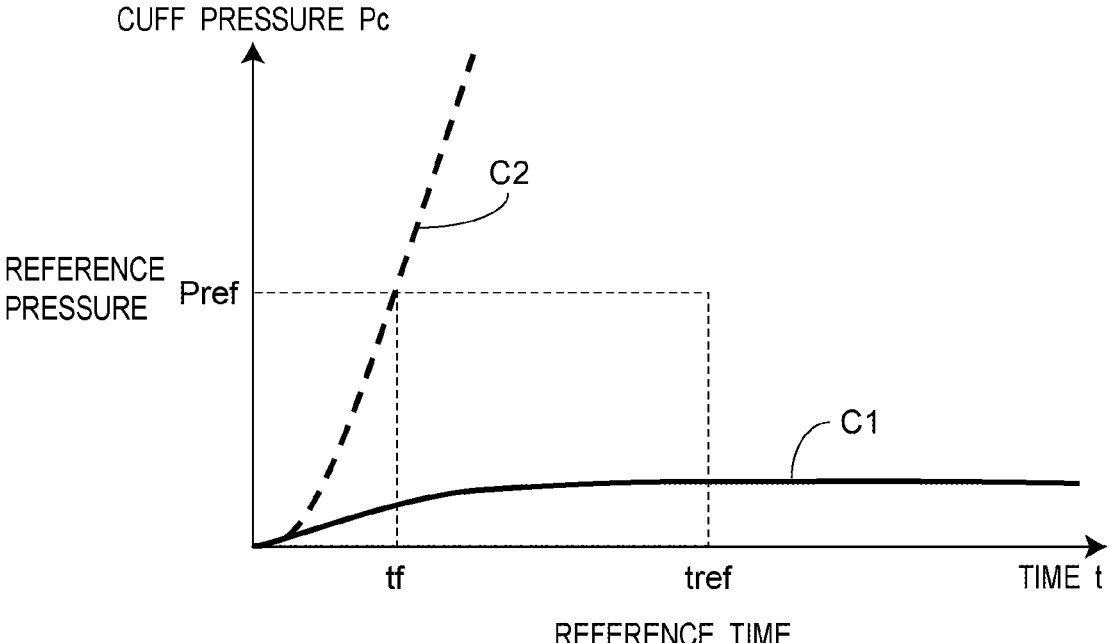
FIG. 9 is a diagram schematically illustrating how to determine whether or not there is an abnormality in the emergency exhaust function according to the degree of increase in the pressure of a cuff in the sphygmomanometer.

(i) For example, as a first case, if the first valve 33 is normal and in a closed state, and the second valve 233 is normal and in an open state, when the fluid is supplied to the cuff 20 by the pump 32, as exemplified as a curved line C1 indicated by a solid line in FIG. 9, the degree of increase in the pressure of the cuff 20 is low because the second valve 233 is in an open state. The second CPU 2100 determines that there is no abnormality in the emergency exhaust function according to the result of "low".

(ii) Next, as a second case, if the first valve 33 is normal and in a closed state, and the second valve 233 is abnormal and in a closed state, when the fluid is supplied to the cuff 20 by the pump 32, as exemplified as a curved line C2 indicated by a broken line in FIG. 9, the degree of increase in the pressure of the cuff 20 is high because the first and second valves 33 and 233 are in a closed state. The second CPU 2100 determines that there is an abnormality in the emergency exhaust function according to the result of "high". In the example in FIG. 9, it is determined that there is an abnormality in the emergency exhaust function at a point of time at which a time tf has elapsed from the start of driving of the pump 32.

(iii) Next, as a third case, if the first valve 33 is abnormal and in an open state, and the second valve 233 is normal and in an open state, when the fluid is supplied to the cuff 20 by the pump 32, the degree of increase in the pressure of the cuff 20 is low because the first valve 33 is in an open state. The second CPU 2100 determines that there is no abnormality in the emergency exhaust function according to the result of "low".

(iv) Finally, as a fourth case, if the first valve 33 is abnormal and in an open state, and the second valve 233 is abnormal and in a closed state, when the fluid is supplied to the cuff 20 by the pump 32, the degree of increase in the pressure of the cuff 20 is low because the first valve 33 is in an open state. The second CPU 2100 determines that there is no abnormality in the emergency exhaust function according to the result of "low".

As a result, in the second case (ii), the CPU 110 can, for example, stop the blood pressure measurement for the measurement target site according to the determination result that there is an abnormality in the emergency exhaust function. Therefore, it is possible to prevent occurrence of a state where the measurement target site remains compressed for a long time. In the example in FIG. 8, the CPU 110 stops the pump 32 (step S208), and gives an opening instruction (de-energization) to the first valve 33 to open the first valve 33 (step S209). At this time, since the first valve 33 is a normally open solenoid valve, it is expected to open in response to the opening instruction. Subsequently, the CPU 110 works as a notification unit, and displays an error indication on the display 50 as a notification that there is an abnormality in the emergency exhaust function (step S210). This error indication may be a message such as "abnormality occurs in emergency exhaust function", or may be an error code such as "Eab" (ab representing numbers set in advance). The notification may be an alarm sound by a buzzer not illustrated. With this notification, the user (typically, the subject) knows that there is an abnormality in the emergency exhaust function, and for example, can take measures such as requesting a service department of a sphygmomanometer manufacturer to perform maintenance service.

On the other hand, in the first case (i), the third case (iii), and the fourth case (iv), the CPU 110 can start blood pressure measurement for the measurement target site according to the determination result that there is no abnormality in the emergency exhaust function. However, in the third case (iii) and the fourth case (iv), since the first valve 33 is abnormal and remains in an open state, the pressure of the cuff 20 does not increase even when the CPU 110 operates the pump 32 to supply the fluid to the cuff 20 for blood pressure measurement. Therefore, it is possible to prevent occurrence of a state where the measurement target site remains compressed for a long time. In this example, since the pressure of the cuff 20 does not increase, the CPU 110 determines that a measurement error has occurred, and stops the blood pressure measurement.

In the first case (i), the CPU 110 can measure the blood pressure of the measurement target site by controlling the operations of the pump 32 and the first and second valves 33 and 233 on the basis of the pressure of the cuff 20 output from the first and second pressure sensors 31 and 231. In this case, since the second valve 233 is normal, emergency exhaust can be performed by making the second valve 233 in an open state in an emergency (in case of emergency).

In the example in FIG. 8, in order to start a blood pressure measurement routine, the CPU 110 once stops the pump 32 (step S206), and gives a closing instruction (de-energization) to the second valve 233 to close the second valve 233 (step S207). At this time, since the second valve 233 is a normally closed solenoid valve, it is expected to close in response to the closing instruction. Thereafter, the process returns to the flow in FIG. 5 and enters into the blood pressure measurement routine (step S3).

(Blood Pressure Measurement Routine)

Figure 7:
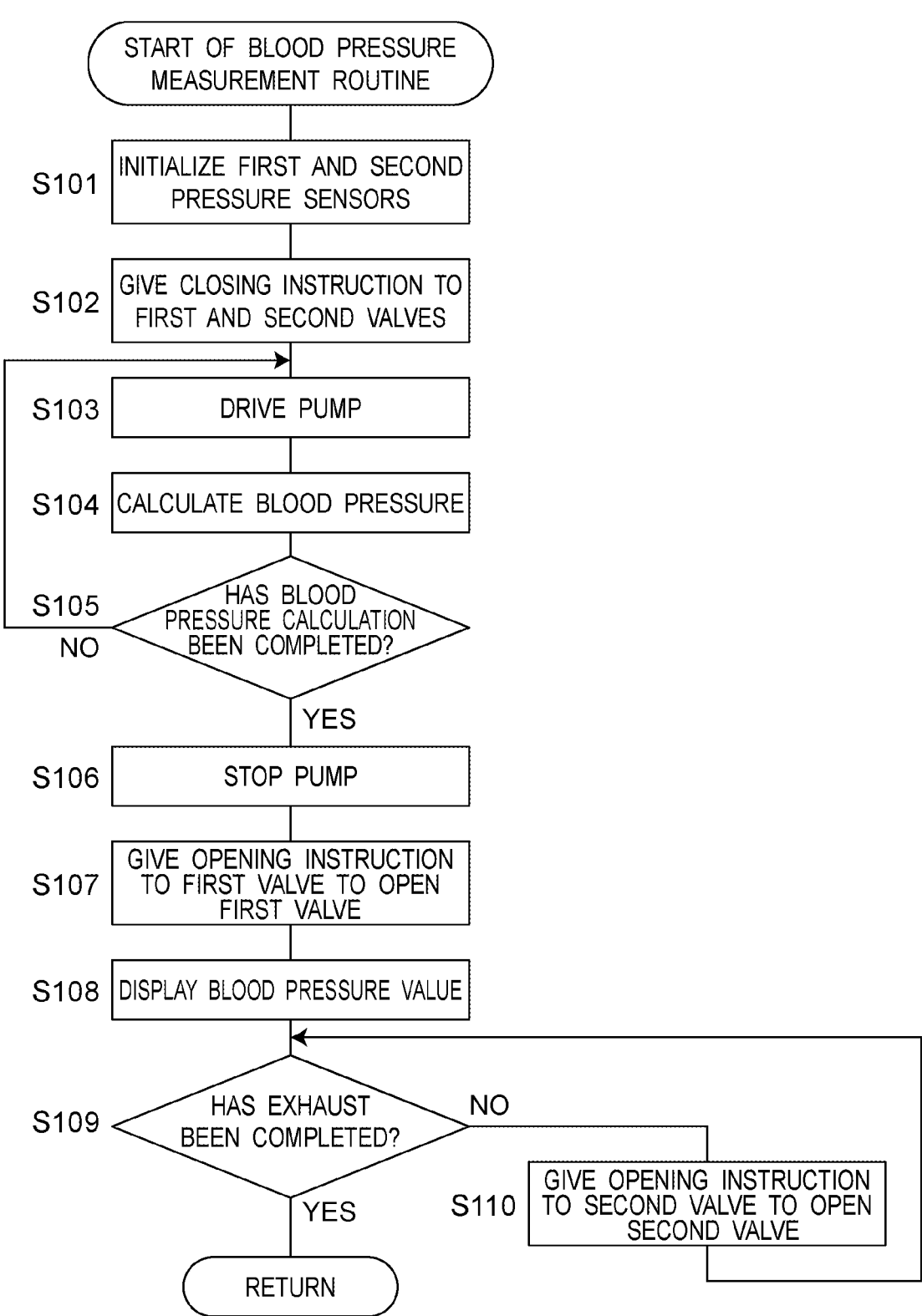
FIG. 7 is a diagram illustrating a specific flow of a blood pressure measurement routine in the operation flows in FIGS. 5 and 6.

As illustrated in FIG. 7, when the process enters into the blood pressure measurement routine, the CPU 110 initializes the first and second pressure sensors 31 and 231 (step S101). Specifically, the CPU 110 initializes a processing memory area and stops the pump 32, and gives an opening instruction (de-energization) and an opening instruction (energization) to the first valve 33 and the second valve 233, respectively. At this time, since the first valve 33 is a normally open solenoid valve, it is expected to open in response to the opening instruction. When either the first valve 33 or the second valve 233 is normal and open, the cuff pressure becomes equal to the atmospheric pressure. In this state, 0 mmHg adjustment (the atmospheric pressure being set to 0 mmHg) of the first pressure sensor 31 and the second pressure sensor 231 is performed.

Next, the CPU 110 gives a closing instruction (energization) to the first valve 33 via the first valve drive circuit 330, and gives a closing instruction (de-energization) to the second valve 233 via the second valve drive circuit 2330 (step S102). At this time, it is unclear whether or not the first valve 33 closes in response to the closing instruction. However, since the second valve 233 is a normally closed solenoid valve, it is expected to close in response to the closing instruction. Subsequently, the CPU 110 drives the pump 32 via the pump drive circuit 320, and starts pressurizing the cuff 20 (fluid bag 22) (step S103). At this time, the CPU 110 controls the pressurization rate of the cuff pressure that is the pressure in the fluid bag 22 on the basis of the output of the first pressure sensor 31 in this example while supplying air from the pump 32 to the fluid bag 22 through the air pipe 39.

Here, if the first valve 33 is abnormal and remains in an open state (the third case (iii) and the fourth case (iv) described above), the pressure of the cuff 20 does not increase even when the CPU 110 operates the pump 32 to supply the fluid to the cuff 20 for the blood pressure measurement. In this example, for example, as indicated by the curved line C1 illustrated in FIG. 9, when the cuff pressure does not become equal to or higher than the reference pressure Pref (in this example, Pref=5 mmHg) even after a lapse of the reference time tref (in this example, tref=5 sec) set in advance from the start of driving of the pump 32, a measurement error occurs, and the subsequent process is stopped (note that the value of the reference time tref and the value of the reference pressure Pref can each be variably set). Therefore, it is possible to prevent occurrence of a state where the measurement target site remains compressed for a long time. Note that, at this time, the CPU 110 may work as a notification unit, and display an error indication on the display 50 as a notification that there is an abnormality in the first valve 33. This error indication may be a message such as "abnormality occurs in valve for blood pressure measurement", or may be an error code such as "Ecd" (cd representing numbers set in advance).

Next, in step S104 in FIG. 7, the CPU 110, particularly the first CPU 1100 works as a blood pressure measurement unit, and attempts to calculate blood pressure values (the maximum blood pressure (systolic blood pressure) and the minimum blood pressure (diastolic blood pressure)) by using an algorithm stored in the memory 51 by a known oscillometric method on the basis of a pulse wave signal (fluctuation component due to a pulse wave included in the output of the first pressure sensor 31) acquired at this point of time.

At this point of time, in a case where the blood pressure values cannot be calculated yet due to lack of data (NO in step S105), the process of steps S103 to S105 is repeated unless the cuff pressure reaches an upper limit pressure (for safety, for example, it is set in advance to 300 mmHg).

When the blood pressure values can be calculated in this manner (YES in step S105), the CPU 110 stops the pump 32 (step S106), and gives an opening instruction (de-energization) to the first valve 33 via the first valve drive circuit 330 (step S107). At this time, since the first valve 33 is a normally open solenoid valve, it is expected to open in response to the opening instruction. Accordingly, control to exhaust the air in the cuff 20 (fluid bag 22) is performed. Furthermore, the CPU 110 displays the calculated blood pressure values on the display 50 (step S108), and performs control to store the blood pressure values in the memory 51.

Thereafter, the CPU 110, particularly the second CPU 2100 determines whether or not the exhaust from the cuff 20 has been completed on the basis of the output of the second pressure sensor 231 (step S109). Specifically, it is determined whether or not the cuff pressure becomes less than the pressure set in advance (for example, 5 mmHg) after a lapse of a time set in advance (for example, 10 seconds) from giving the opening instruction (de-energization) to the first valve 33. Here, if the exhaust from the cuff 20 is not completed for some reason (NO in step S109), the second CPU 2100 gives an opening instruction (energization) to the second valve 233 via the second valve drive circuit 2330 (step S110). Here, it has been confirmed that the second valve 233 does not become abnormal and a closed state (the second case (ii) described above) in the immediately preceding operation confirmation routine of the protection device unit (FIG. 8). Therefore, the second valve 233 is reliably expected to open in response to the opening instruction (energization). Accordingly, the exhaust from the cuff 20 can be reliably completed.

When the exhaust from the cuff 20 is completed (YES in step S109), the process returns to the operation flow in FIG. 5. In the example in FIG. 5, the operation flow ends as it is.

In this manner, according to the sphygmomanometer 100, it is possible to reliably prevent occurrence of a state where the measurement target site remains compressed for a long time.

Furthermore, in the operation flow in FIG. 5, the second CPU 2100 performs the operation confirmation routine of the protection device unit (step S2) prior to the blood pressure measurement routine (step S3) each time the first CPU 1100 performs the blood pressure measurement routine. Therefore, it is possible to further reliably prevent occurrence of a state where the measurement target site remains compressed for a long time.

Furthermore, in the sphygmomanometer 100, the first valve 33 and the second valve 233 are valves of types different from each other (normally open valve and normally closed valve). Accordingly, the probability of occurrence of an abnormality due to the same failure is low as compared with a case of valves of the same type. Therefore, the reliability of the sphygmomanometer 100 as a product can be enhanced. Furthermore, the first valve 33 for blood pressure measurement is a normally open solenoid valve. Accordingly, it is sufficient that the first valve 33 becomes a closed state upon receiving a closing instruction (actuation instruction, that is, energization) during the blood pressure measurement (a period in which the measurement target site is temporarily compressed by the cuff 20), and it is sufficient that the first valve 33 is not actuated (de-energized) and in an open state during a period other than during the blood pressure measurement. The second valve 233 for emergency exhaust is a normally closed solenoid valve. Accordingly, it is sufficient that the second valve 233 becomes an open state upon receiving an opening instruction (actuation instruction, that is, energization) during the emergency exhaust, and it is sufficient that the second valve 233 is not actuated (de-energized) and in a closed state during a period other than during the emergency exhaust. Therefore, the power consumption of the first valve 33 and the second valve 233 can be reduced.

(Case where Abnormality Determination of Emergency Exhaust Function is Performed Only in Nighttime Blood Pressure Measurement Mode)

FIG. 6 illustrates an operation flow in a case where the sphygmomanometer 100 performs determination of the presence or absence of the abnormality of the emergency exhaust function only in the nighttime blood pressure measurement mode. It is assumed that the sphygmomanometer 100 is powered on at the start of the flow, and in the regular blood pressure measurement mode.

As illustrated in FIG. 4B, it is assumed that the user 80 wearing the sphygmomanometer 100 on the left wrist 90 is in a posture of the supine position.

As shown in step S11 in FIG. 6, when the user presses down the nighttime measurement switch 52B provided on the main body 10, in this example, the sphygmomanometer 100 transitions from the regular blood pressure measurement mode to the nighttime blood pressure measurement mode in response to the pressing down. In this example, in the nighttime blood pressure measurement mode, it is assumed that a schedule is established to measure once every two hours until, for example, 7:00 a.m. after the nighttime measurement switch 52B is pressed. Note that the schedule is not limited to this schedule, and may be established to measure at fixed clock times such as 1:00 a.m., 2:00 a.m., 3:00 a.m., or the like until, for example, 7:00 a.m. after the nighttime measurement switch 52B is pressed.

Next, as shown in step S12 in FIG. 6, the CPU 110 determines whether or not it is the measurement clock time set in the schedule (for the nighttime blood pressure measurement mode). If it is not the measurement clock time set in the schedule (NO in step S12), the CPU 110 waits for the measurement clock time set in the schedule.

When the measurement clock time set in the schedule is reached (YES in step S12), as shown in step S13 in FIG. 6, the CPU 110 executes the operation confirmation routine of the protection device unit similarly to step S2 in FIG. 5. That is, the CPU 110, particularly the second CPU 2100 works as an abnormality determination unit, and performs a determination process of determining whether or not there is an abnormality in the emergency exhaust function according to the degree of increase in the pressure of the cuff 20. Here, if there is an abnormality in the emergency exhaust function, the CPU 110 stops the blood pressure measurement for the measurement target site, and displays an error indication that there is an abnormality in the emergency exhaust function on the display 50 (in particular, steps S208 to S210 in FIG. 8).

On the other hand, if there is no abnormality in the emergency exhaust function, as shown in step S14 in FIG. 6, the blood pressure measurement routine is executed similarly to step S3 in FIG. 5. That is, the CPU 110, particularly the first CPU 1100 works as a blood pressure measurement unit, performs calculation of blood pressure values (the maximum blood pressure (systolic blood pressure) and the minimum blood pressure (diastolic blood pressure)) by using an algorithm stored in the memory 51 by a known oscillometric method on the basis of a pulse wave signal (fluctuation component due to a pulse wave included in the output of the first pressure sensor 31), and displays the calculated blood pressure values on the display 50, or the like (in particular, steps S101 to S108 in FIG. 7). Subsequently, if the exhaust from the cuff 20 is not completed for some reason (NO in step S109 in FIG. 7), the CPU 110, particularly the second CPU 2100 gives an opening instruction (energization) to the second valve 233 via the second valve drive circuit 2330 (step S110). Accordingly, the exhaust from the cuff 20 is reliably completed.

When one blood pressure measurement set in the schedule is completed in this manner, in step S15, the CPU 110 determines whether or not all the blood pressure measurement set in the schedule has been completed. Here, as long as the blood pressure measurement is still scheduled according to the schedule (NO in step S15), the CPU 110 waits for the next measurement clock time set in the schedule.

When the next measurement clock time set in the schedule is reached (YES in step S12), the CPU 110 repeats the process of steps S13 to S15. Furthermore, in step S15, the CPU 110 determines whether or not all the blood pressure measurement set in the schedule has been completed. When all the blood pressure measurement set in the schedule is completed in this manner (YES in step S15), the CPU 110 ends the nighttime blood pressure measurement mode.

In the nighttime blood pressure measurement mode, if the second valve 233 for emergency exhaust is failed in an emergency (in case of emergency), a state occurs where the measurement target site remains compressed for a long time while the subject is unconscious. Such a situation should reliably be prevented. Therefore, in the operation flow in FIG. 6, in the nighttime blood pressure measurement mode, the second CPU 2100 performs the operation confirmation routine of the protection device unit (step S13) prior to the blood pressure measurement routine (step S14) each time the first CPU 1100 performs the blood pressure measurement routine. Therefore, it is possible to further reliably prevent occurrence of a state where the measurement target site remains compressed for a long time.

On the other hand, in the operation flow in FIG. 6, the regular blood pressure measurement mode is maintained unless the nighttime measurement switch 52B is pressed down (NO in step S11). In this case, the CPU 110, when the measurement switch 52A is pressed down (YES in step S21), the CPU 110 proceeds to step S22 in response to the input blood pressure measurement instruction without entering into the operation confirmation routine of the protection device unit (FIG. 8) (in short, without performing the determination process described above (steps S204 and S205)), and executes the blood pressure measurement routine. Accordingly, the blood pressure of the measurement target site is measured.

The reason for omitting the operation confirmation routine of the protection device unit (FIG. 8) in the regular blood pressure measurement mode (steps S21 to S22) in the operation flow in FIG. 6 in this manner is as follows. Firstly, this is because, in the regular blood pressure measurement mode, if the operation confirmation routine of the protection device unit is performed prior to the blood pressure measurement routine each time the first CPU 1100 performs the blood pressure measurement routine, a time period required for one blood pressure measurement (here, it means a total time period of a time period required for the operation confirmation routine of the protection device unit and a time period required for an actual blood pressure measurement routine) becomes long as a whole. Secondly, this is because, in the regular blood pressure measurement mode, the subject is in an awake state, thus it can be said that performing the operation confirmation routine of the protection device unit (in short, the determination process described above (steps S204 and S205)) is less significant than in the nighttime blood pressure measurement mode.

In the embodiment described above, a blood pressure measurement unit and the abnormality determination unit are constituted of a programmed first CPU 1100 and a programmed second CPU 2100 different from the first CPU 1100. In addition, the first valve 33 is driven by the first CPU 1100 via the first valve drive circuit 330, and the second valve 233 is driven by the second CPU 2100 via the second valve drive circuit 2330. Therefore, even when an abnormality has occurred in either one of a set of the first CPU 1100, the first valve drive circuit 330, and the first valve 33 or a set of the second CPU 2100, the second valve drive circuit 2330, and the second valve 233, if the other set is normal, the exhaust from the cuff 20 can be performed. Therefore, it is possible to further reliably prevent occurrence of a state where the measurement target site remains compressed for a long time.

(Modification)

In the operation flow in FIG. 6, as shown in step S11, when the user presses down the nighttime measurement switch 52B provided on the main body 10, the sphygmomanometer 100 immediately transitions from the regular blood pressure measurement mode to the nighttime blood pressure measurement mode in response to the pressing down. However, the present invention is not limited thereto. For example, when the user presses down the nighttime measurement switch 52B provided on the main body 10 (step S11), the CPU 110 may first execute the operation confirmation routine of the protection device unit (FIG. 8) in response to the pressing down. Then, when determining that there is an abnormality in the emergency exhaust function, the CPU 100 may prohibit the sphygmomanometer 100 from transitioning to the nighttime blood pressure measurement mode, while when determining that there is no abnormality in the emergency exhaust function, the CPU 110 may allow the sphygmomanometer to transition to the nighttime blood pressure measurement mode. Accordingly, it is possible to further reliably prevent a situation in which a state occurs where the measurement target site remains compressed for a long time while the subject is unconscious.

In the embodiment described above, the first valve 33 is a normally open solenoid valve, and the second valve 233 is a normally closed solenoid valve, but the present invention is not limited thereto. The types of the first valve 33 and the second valve 233 (the normally open valve and the normally closed valve) may be any type.

Furthermore, the sphygmomanometer 100 is of a type that compresses a wrist (the left wrist 90 in the above example, but may be a right wrist) as the measurement target site. Accordingly, it is expected that the degree of disturbing the sleep of the user (subject) is less than that in a type that compresses an upper arm (Imai et al., "Development and evaluation of a home nocturnal blood pressure monitoring system using a wrist-cuff device", Blood Pressure Monitoring 2018, 23, P318-326). Therefore, the sphygmomanometer 100 is suitable for nighttime blood pressure measurement.

Furthermore, the sphygmomanometer 100 is integrally and compactly formed as a wrist-type sphygmomanometer. Accordingly, handling by a user becomes convenient.

Furthermore, in the embodiment described above, a blood pressure is calculated in the pressurization process of the cuff 20 (fluid bag 22), but the present invention is not limited thereto. The blood pressure may be calculated in a depressurization process of the cuff 20.

Furthermore, in the embodiment described above, the measurement switch 52A and the nighttime measurement switch 52B each provided on the main body 10 are provided as the operation unit, but the present invention is not limited thereto. The operation unit may be constituted of, for example, a communication unit that receives an instruction from a smartphone or the like existing outside the sphygmomanometer 100 via wireless communication.

Furthermore, in the embodiment described above, the main body 10 is provided integrally with the cuff 20, but the present invention is not limited thereto. The main body 10 may be formed as a separate body from the cuff 20, and may be connected to the cuff 20 (fluid bag 22) via a flexible air tube so as to be capable of fluid communication.

The above-described blood pressure measurement method (in particular, the operation flow of FIGS. 5-8) may be recorded as software (a computer program) on a non-transitory recording medium capable of storing data, such as a compact disc (CD), a digital universal disc (DVD), or a flash memory. By installing software recorded on such a recording medium in a substantial computer device such as a personal computer, a personal digital assistant (PDA), or a smartphone, the computer device can be caused to execute the above-described blood pressure measurement method.

As described above, a sphygmomanometer of the present disclosure is a sphygmomanometer that performs blood pressure measurement by temporarily compressing a measurement target site by a blood pressure measurement cuff, the sphygmomanometer comprising:

a pump that supplies a fluid to the cuff to pressurize the cuff;

a pressure sensor that detects a pressure of the cuff;

a first valve for regular measurement that discharges the fluid from the cuff to depressurize the cuff during blood pressure measurement;

a second valve for emergency exhaust that discharges the fluid from the cuff to depressurize the cuff when an abnormality occurs in which discharge of the fluid by the first valve is not normally performed;

a blood pressure measurement unit that controls operations of the pump and the first and second valves on a basis of the pressure of the cuff output from the pressure sensor to measure a blood pressure of the measurement target site; and an abnormality determination unit that performs a determination process of supplying the fluid to the cuff by the pump in a state where a closing instruction is given to the first valve and an opening instruction is given to the second valve, and determining whether or not there is an abnormality in an emergency exhaust function according to a degree of increase in the pressure of the cuff.

In this specification, giving a "closing instruction" to a valve refers to controlling the valve to close regardless of whether the valve type is a normally open valve or a normally closed valve. Furthermore, giving an "opening instruction" to a valve refers to controlling the valve to open regardless of whether the valve type is a normally open valve or a normally closed valve.

In the sphygmomanometer of the present disclosure, the abnormality determination unit supplies the fluid to the cuff by the pump in a state where a closing instruction is given to the first valve and an opening instruction is given to the second valve. In this case:

(i) For example, as a first case, if the first valve is normal and in a closed state, and the second valve is normal and in an open state, when the fluid is supplied to the cuff by the pump, the degree of increase in the pressure of the cuff is low because the second valve is in an open state. The abnormality determination unit determines that there is no abnormality in the emergency exhaust function according to the result of "low".

(ii) Next, as a second case, if the first valve is normal and in a closed state, and the second valve is abnormal and in a closed state, when the fluid is supplied to the cuff by the pump, the degree of increase in the pressure of the cuff is high because the first and second valves are in a closed state. The abnormality determination unit determines that there is an abnormality in the emergency exhaust function according to the result of "high".

(iii) Next, as a third case, if the first valve is abnormal and in an open state, and the second valve is normal and in an open state, when the fluid is supplied to the cuff by the pump, the degree of increase in the pressure of the cuff is low because the first valve is in an open state. The abnormality determination unit determines that there is no abnormality in the emergency exhaust function according to the result of "low".

(iv) Finally, as a fourth case, if the first valve is abnormal and in an open state, and the second valve is abnormal and in a closed state, when the fluid is supplied to the cuff by the pump, the degree of increase in the pressure of the cuff is low because the first valve is in an open state. The abnormality determination unit determines that there is no abnormality in the emergency exhaust function according to the result of "low".

As a result, in the second case, the blood pressure measurement unit can, for example, stop the blood pressure measurement for the measurement target site according to the determination result that there is an abnormality in the emergency exhaust function. Therefore, it is possible to prevent occurrence of a state where the measurement target site remains compressed for a long time. On the other hand, in the first case, the third case, and the fourth case, the blood pressure measurement unit can start blood pressure measurement for the measurement target site according to the determination result that there is no abnormality in the emergency exhaust function. However, in the third case and the fourth case, since the first valve is abnormal and remains in an open state, the pressure of the cuff does not increase even when the blood pressure measurement unit operates the pump to supply the fluid to the cuff (typically, a measurement error occurs). Therefore, it is possible to prevent occurrence of a state where the measurement target site remains compressed for a long time. In the first case, the blood pressure measurement unit can measure the blood pressure of the measurement target site by controlling the operations of the pump and the first and second valves on the basis of the pressure of the cuff output from the pressure sensor. In this case, since the second valve is normal, emergency exhaust can be performed by making the second valve in an open state in an emergency (in case of emergency). In this manner, according to the sphygmomanometer, it is possible to reliably prevent occurrence of a state where the measurement target site remains compressed for a long time.

In the sphygmomanometer according to one embodiment, the abnormality determination unit performs the determination process prior to the blood pressure measurement each time the blood pressure measurement unit performs the blood pressure measurement.

In the sphygmomanometer according to this one embodiment, the abnormality determination unit performs the determination process prior to the blood pressure measurement each time the blood pressure measurement unit performs the blood pressure measurement. Therefore, it is possible to further reliably prevent occurrence of a state where the measurement target site remains compressed for a long time.

In the sphygmomanometer according to one embodiment, when the abnormality determination unit determines that there is an abnormality in the emergency exhaust function, the blood pressure measurement unit stops the blood pressure measurement for the measurement target site, while when the abnormality determination unit determines that there is no abnormality in the emergency exhaust function, the blood pressure measurement unit starts the blood pressure measurement.

In the sphygmomanometer according to this one embodiment, when the abnormality determination unit determines that there is an abnormality in the emergency exhaust function, the blood pressure measurement unit stops the blood pressure measurement for the measurement target site. Therefore, it is possible to reliably prevent occurrence of a state where the measurement target site remains compressed for a long time. On the other hand, when the abnormality determination unit determines that there is no abnormality in the emergency exhaust function, the blood pressure measurement unit starts the blood pressure measurement. Here, in the third case and the fourth case, since the first valve is abnormal and remains in an open state, the pressure of the cuff does not increase even when the blood pressure measurement unit operates the pump to supply the fluid to the cuff. Therefore, the blood pressure measurement unit can determine that the first valve is abnormal and a measurement error has occurred according to the degree of increase in the pressure of the cuff, and can stop the measurement according to the determination result. In the first case, when the blood pressure measurement unit operates the pump to supply the fluid to the cuff, the pressure of the cuff increases normally, so that the blood pressure measurement unit can complete the blood pressure measurement.

In the sphygmomanometer according to one embodiment, the first valve is a normally open valve, and the second valve is a normally closed valve.

In the sphygmomanometer according to this one embodiment, the first valve and the second valve are valves of types different from each other (normally open valve and normally closed valve). Accordingly, the probability of occurrence of an abnormality due to the same failure is low as compared with a case of valves of the same type. Therefore, the reliability of the sphygmomanometer as a product can be enhanced. Furthermore, the first valve for blood pressure measurement is a normally open solenoid valve. Accordingly, it is sufficient that the first valve becomes a closed state upon receiving a closing instruction (actuation instruction) during the blood pressure measurement (a period in which the measurement target site is temporarily compressed by the blood pressure measurement cuff), and it is sufficient that the first valve is not actuated and in an open state during a period other than during the blood pressure measurement. The second valve for emergency exhaust is a normally closed solenoid valve. Accordingly, it is sufficient that the second valve becomes an open state upon receiving an opening instruction (actuation instruction) during the emergency exhaust, and it is sufficient that the second valve is not actuated and in a closed state during a period other than during the emergency exhaust. Therefore, the power consumption of the first valve and the second valve can be reduced.

The sphygmomanometer according to one embodiment comprises an automatic measurement mode in which the blood pressure measurement is automatically started according to a schedule set in advance, wherein
in the automatic measurement mode, the abnormality determination unit performs the determination process prior to the blood pressure measurement each time the blood pressure measurement unit performs the blood pressure measurement according to the schedule.

In the automatic measurement mode, if the second valve for emergency exhaust is failed in an emergency (in case of emergency), there is a possibility that a state occurs in which the measurement target site remains compressed for a long time. Therefore, in the sphygmomanometer according to this one embodiment, in the automatic measurement mode, the abnormality determination unit performs the determination process prior to the blood pressure measurement each time the blood pressure measurement unit performs the blood pressure measurement according to the schedule. Therefore, it is possible to reliably prevent a situation in which a state occurs where the measurement target site remains compressed for a long time while the subject is unconscious.

The sphygmomanometer according to one embodiment comprises a regular blood pressure measurement mode in which the blood pressure measurement is performed in response to an input blood pressure measurement instruction, wherein in the regular blood pressure measurement mode, the abnormality determination unit does not perform the determination process, and the blood pressure measurement unit measures the blood pressure of the measurement target site in response to the input blood pressure measurement instruction.

In the regular blood pressure measurement mode, if the abnormality determination unit performs the determination process prior to the blood pressure measurement each time the blood pressure measurement unit performs the blood pressure measurement, a time period required for one blood pressure measurement (here, it means a total time period of a time period required for the determination process and a time period required for an actual blood pressure measurement) becomes long as a whole. On the other hand, in the regular blood pressure measurement mode, since the measurement subject is in an awake state, it can be said that performing the determination process is less significant than in a case where the measurement of the blood pressure is started according to the schedule set in advance while a subject is sleeping (nighttime) as in the nighttime sphygmomanometer, for example. Therefore, in the sphygmomanometer according to this one embodiment, in the regular blood pressure measurement mode, the abnormality determination unit does not perform the determination process, and the blood pressure measurement unit measures the blood pressure of the measurement target site in response to the input blood pressure measurement instruction. Therefore, the time required for one blood pressure measurement becomes short as a whole as compared with the case where the abnormality determination unit performs the determination process prior to the blood pressure measurement each time the blood pressure measurement unit performs the blood pressure measurement.

In the sphygmomanometer according to one embodiment, when a transition instruction to transition to the automatic measurement mode is input, the abnormality determination unit performs the determination process in response to the transition instruction, and when determining that there is an abnormality in the emergency exhaust function, the abnormality determination unit prohibits the sphygmomanometer from transitioning to the automatic measurement mode, while when determining that there is no abnormality in the emergency exhaust function, the abnormality determination unit allows the sphygmomanometer to transition to the automatic measurement mode.

In the sphygmomanometer according to this one embodiment, when a transition instruction to transition to the automatic measurement mode is input, the abnormality determination unit performs the determination process in response to the transition instruction. Then, when determining that there is an abnormality in the emergency exhaust function, the abnormality determination unit prohibits the sphygmomanometer from transitioning to the automatic measurement mode, while when determining that there is no abnormality in the emergency exhaust function, the abnormality determination unit allows the sphygmomanometer to transition to the automatic measurement mode. Therefore, it is possible to further reliably prevent a situation in which a state occurs where the measurement target site remains compressed for a long time while the subject is unconscious.

Note that, the "transition instruction" to transition to the automatic measurement mode is input via, for example, a switch as an operation unit provided on the main body of the sphygmomanometer.

The sphygmomanometer according to one embodiment comprises a notification unit that notifies that there is an abnormality in the emergency exhaust function when the abnormality determination unit determines that there is an abnormality in the emergency exhaust function.

In the sphygmomanometer according to this one embodiment, when the abnormality determination unit determines that there is an abnormality in the emergency exhaust function, the notification unit notifies that there is an abnormality in the emergency exhaust function. With this notification, the user (typically, the subject) knows that there is an abnormality in the emergency exhaust function, and for example, can take measures such as requesting a service department of a sphygmomanometer manufacturer to perform maintenance service.

In the sphygmomanometer according to one embodiment, the blood pressure measurement unit and the abnormality determination unit are constituted of a programmed first processor and a programmed second processor different from the first processor, the first valve is driven by the first processor, and the second valve is driven by the second processor.

In the sphygmomanometer according to this one embodiment, even when an abnormality has occurred in either one of a set of the first processor and the first valve or a set of the second processor and the second valve, if the other set is normal, the exhaust from the cuff can be performed. Therefore, it is possible to further reliably prevent occurrence of a state where the measurement target site remains compressed for a long time.

In another aspect, a blood pressure measurement method of the present disclosure is a blood pressure measurement method for performing blood pressure measurement by temporarily compressing a measurement target site by a blood pressure measurement cuff, comprising:

a pump that supplies a fluid to the cuff to pressurize the cuff;

a pressure sensor that detects a pressure of the cuff;

a first valve for regular measurement that discharges the fluid from the cuff to depressurize the cuff during blood pressure measurement; and a second valve for emergency exhaust that discharges the fluid from the cuff to depressurize the cuff when an abnormality occurs in which discharge of the fluid by the first valve is not normally performed, the blood pressure measurement method comprising:

a measurement step of measuring a blood pressure of the measurement target site by controlling operations of the pump and the first and second valves on a basis of the pressure of the cuff output from the pressure sensor; and a determination step of supplying the fluid to the cuff by the pump in a state where a closing instruction is given to the first valve and an opening instruction is given to the second valve, and determining whether or not there is an abnormality in an emergency exhaust function according to a degree of increase in the pressure of the cuff, as a step performed prior to the measurement step each time the measurement step is performed.

According to the blood pressure measurement method of the present disclosure, it is possible to reliably prevent occurrence of a state where the measurement target site remains compressed for a long time.

In yet another aspect, a computer-readable recording medium according to the present disclosure is a non-transitorily computer-readable recording medium storing a program for causing a computer to execute the above blood pressure measurement method.

By making a computer read the program stored in the computer-readable recording medium according to the present disclosure and causing a computer to execute the program, the blood pressure measurement method can be implemented.

As is clear from the above, according to the sphygmomanometer and the blood pressure measurement method of the present disclosure, it is possible to reliably prevent occurrence of a state where the measurement target site remains compressed for a long time. Furthermore, according to the program stored in the computer-readable recording medium of the present disclosure, it is possible to cause a computer to implement such a blood pressure measurement method.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer that performs blood pressure measurement by temporarily compressing a measurement target site by a blood pressure measurement cuff, the sphygmomanometer comprising:

a pump that supplies a fluid to the cuff to pressurize the cuff;

a pressure sensor that detects a pressure of the cuff;

a first valve for regular measurement that is fluid-communicatively connected to the cuff and discharges the fluid from the cuff to depressurize the cuff during blood pressure measurement;

a second valve for emergency exhaust that is fluid-communicatively connected to the cuff and discharges the fluid from the cuff to depressurize the cuff when an abnormality occurs in which discharge of the fluid by the first valve is not normally performed;

a blood pressure measurement unit that controls operations of the pump and the first and second valves on a basis of the pressure of the cuff output from the pressure sensor to measure a blood pressure of the measurement target site; and an abnormality determination unit that performs a determination process of determining whether or not there is an abnormality in an emergency exhaust function, wherein the abnormality determination unit is configured to, prior to the blood pressure measurement by the blood pressure measurement unit, supply the fluid to the cuff by the pump in a state where a closing instruction is given to the first valve and an opening instruction is given to the second valve, and, if the pressure of the cuff becomes equal to or higher than a first reference pressure within a first reference time from a start of driving of the pump, determine that the second valve is abnormal and that there is an abnormality in the emergency exhaust function, whereas if the pressure of the cuff remains lower than the first reference pressure until the first reference time elapses from the start of driving of the pump, determine that there is no abnormality in the emergency exhaust function regardless of whether the first valve is normal or abnormal, and the blood pressure measurement unit is configured to, upon start of blood pressure measurement, supply the fluid to the cuff by the pump in a state where closing instructions are given to both the first valve and the second valve, and, if the pressure of the cuff does not become equal to or higher than a second reference pressure within a second reference time from the start of driving of the pump, determine that a measurement error has occurred.

2. The sphygmomanometer according to claim 1, wherein the abnormality determination unit performs the determination process prior to the blood pressure measurement each time the blood pressure measurement unit performs the blood pressure measurement.

3. The sphygmomanometer according to claim 1, wherein when the abnormality determination unit determines that there is an abnormality in the emergency exhaust function, the blood pressure measurement unit stops the blood pressure measurement for the measurement target site, while when the abnormality determination unit determines that there is no abnormality in the emergency exhaust function, the blood pressure measurement unit starts the blood pressure measurement.

4. The sphygmomanometer according to claim 1, wherein the first valve is a normally open valve that is open in its resting state until closed, and the second valve is a normally closed valve that is closed in its resting state until open.

5. The sphygmomanometer according to claim 1, comprising an automatic measurement mode in which the blood pressure measurement is automatically started according to a schedule set in advance, wherein in the automatic measurement mode, the abnormality determination unit performs the determination process prior to the blood pressure measurement each time the blood pressure measurement unit performs the blood pressure measurement according to the schedule.

6. The sphygmomanometer according to claim 5, comprising a regular blood pressure measurement mode in which the blood pressure measurement is performed in response to an input blood pressure measurement instruction, wherein in the regular blood pressure measurement mode, the abnormality determination unit does not perform the determination process, and the blood pressure measurement unit measures the blood pressure of the measurement target site in response to the input blood pressure measurement instruction.

7. The sphygmomanometer according to claim 5, wherein when a transition instruction to transition to the automatic measurement mode is input, the abnormality determination unit performs the determination process in response to the transition instruction, and when determining that there is an abnormality in the emergency exhaust function, the abnormality determination unit prohibits the sphygmomanometer from transitioning to the automatic measurement mode, while when determining that there is no abnormality in the emergency exhaust function, the abnormality determination unit allows the sphygmomanometer to transition to the automatic measurement mode.

8. The sphygmomanometer according to claim 1, comprising a notification unit that notifies that there is an abnormality in the emergency exhaust function when the abnormality determination unit determines that there is an abnormality in the emergency exhaust function.

9. The sphygmomanometer according to claim 1, wherein the blood pressure measurement unit and the abnormality determination unit are constituted of a programmed first processor and a programmed second processor different from the first processor, the first valve is driven by the first processor, and the second valve is driven by the second processor.

10. A blood pressure measurement method for performing blood pressure measurement by the sphygmomanometer according to claim 1, comprising:

the blood pressure measurement method comprising:

a determination step by the abnormality determination unit of, prior to blood pressure measurement by the blood pressure measurement unit, supplying the fluid to the cuff by the pump in the state where the closing instruction is given to the first valve and the opening instruction is given to the second valve, and, if the pressure of the cuff becomes equal to or higher than the first reference pressure within the first reference time from the start of driving of the pump, determining that the second valve is abnormal and that there is the abnormality in the emergency exhaust function, whereas if the pressure of the cuff remains lower than the first reference pressure until the first reference time elapses from the start of driving of the pump, determining that there is no abnormality in the emergency exhaust function regardless of whether the first valve is normal or abnormal; and a measurement step by the blood pressure measurement unit of, upon start of blood pressure measurement by the blood pressure measurement unit, supplying the fluid to the cuff by the pump in the state where closing instructions are given to both the first valve and the second valve, and, if the pressure of the cuff does not become equal to or higher than the second reference pressure within the second reference time from the start of driving of the pump, determining that the measurement error has occurred, whereas if the pressure of the cuff becomes equal to or higher than the second reference pressure within the second reference time from the start of driving of the pump, measuring a blood pressure of the measurement target site by controlling operations of the pump and the first and second valves on a basis of the pressure of the cuff output from the pressure sensor.

11. A non-transitory computer-readable recording medium storing a program for causing a computer to execute the blood pressure measurement method according to claim 10.

12. A sphygmomanometer that performs blood pressure measurement by temporarily compressing a measurement target site by a blood pressure measurement cuff, the sphygmomanometer comprising:

a pump that supplies a fluid to the cuff to pressurize the cuff;

a pressure sensor that detects a pressure of the cuff;

a first valve for regular measurement that discharges the fluid from the cuff to depressurize the cuff during blood pressure measurement;

a second valve for emergency exhaust that discharges the fluid from the cuff to depressurize the cuff when an abnormality occurs in which discharge of the fluid by the first valve is not normally performed;

a blood pressure measurement unit that controls operations of the pump and the first and second valves on a basis of the pressure of the cuff output from the pressure sensor to measure a blood pressure of the measurement target site;

an abnormality determination unit that performs a determination process of supplying the fluid to the cuff by the pump in a state where a closing instruction is given to the first valve and an opening instruction is given to the second valve, and determining whether or not there is an abnormality in an emergency exhaust function according to a degree of increase in the pressure of the cuff; and an automatic measurement mode in which the blood pressure measurement is automatically started according to a schedule set in advance, wherein when a transition instruction to transition to the automatic measurement mode is input, the abnormality determination unit performs the determination process in response to the transition instruction, and when determining that there is an abnormality in the emergency exhaust function, the abnormality determination unit prohibits the sphygmomanometer from transitioning to the automatic measurement mode, while when determining that there is no abnormality in the emergency exhaust function, the abnormality determination unit allows the sphygmomanometer to transition to the automatic measurement mode.

* * * * *